United States Patent
McAllister et al.

(10) Patent No.: US 12,279,028 B2
(45) Date of Patent: Apr. 15, 2025

(54) IMAGE SENSOR AND THERMAL CAMERA DEVICE, SYSTEM AND METHOD

(71) Applicant: AgEagle Aerial, Inc., Wichita, KS (US)

(72) Inventors: Justin McAllister, Seattle, WA (US); Jefferson McBride, Edmonds, WA (US); Gabriel Eduardo Torres, Seattle, WA (US); David Swartzendruber, Seattle, WA (US)

(73) Assignee: AgEagle Aerial, Inc., Wichita, KS (US)

( * ) Notice: Subject to any disclaimer, the term of this patent is extended or adjusted under 35 U.S.C. 154(b) by 0 days.

(21) Appl. No.: 18/744,539

(22) Filed: Jun. 14, 2024

(65) Prior Publication Data

US 2025/0088721 A1 Mar. 13, 2025

Related U.S. Application Data

(63) Continuation of application No. 17/299,258, filed as application No. PCT/US2019/064296 on Dec. 3, 2019, now Pat. No. 12,028,588.

(60) Provisional application No. 62/774,812, filed on Dec. 3, 2018, provisional application No. 62/774,814, filed on Dec. 3, 2018, provisional application No. 62/774,815, filed on Dec. 3, 2018.

(51) Int. Cl.
*G06T 7/00* (2017.01)
*G01J 3/28* (2006.01)
(Continued)

(52) U.S. Cl.
CPC ............ *H04N 23/11* (2023.01); *G01J 3/2823* (2013.01); *G01J 5/02* (2013.01); *G06T 7/97* (2017.01);
(Continued)

(58) Field of Classification Search
CPC ........ H04N 23/11; G06T 7/97; G06V 20/188; G01J 3/2823; G01J 5/02
See application file for complete search history.

(56) References Cited

U.S. PATENT DOCUMENTS

| | | | | |
|---|---|---|---|---|
| 5,467,271 A | * | 11/1995 | Abel | A01B 79/005 |
| | | | | 702/5 |
| 5,471,056 A | * | 11/1995 | Prelat | G01V 8/02 |
| | | | | 250/252.1 |

(Continued)

FOREIGN PATENT DOCUMENTS

| BR | 9303870 A | 3/1994 |
|---|---|---|
| CN | 1802891 A | 7/2006 |

(Continued)

OTHER PUBLICATIONS

Panagiotopoulou et al., "Super-Resolution Reconstruction of Thermal Infrared Images," *Proceedings of the 4th WSEAS International Conference on Remote Sensing*, Patras, Greece, Nov. 2008, pp. 40-44.

*Primary Examiner* — Edward Park
(74) *Attorney, Agent, or Firm* — Seed IP Law Group LLP

(57) ABSTRACT

The present disclosure is directed to devices and methods for synchronizing capturing of spectral images with the capturing of thermal images. A thermal imaging device of an aerial vehicle captures a sequence of thermal image of thermal images. Capturing of spectral images by a spectral imaging device of the aerial vehicle is synchronized with the capturing of the thermal images. Irradiance data indicative of a background temperature is sensed. A digital surface model of an area of interest is generated based on the sequence of spectral images. An emissivity of a target is estimated and a temperature of a pixel of the digital surface model of the target is estimated based on the sequence of thermal images, the irradiance data indicative of the background temperature and the estimated emissivity of the target.

20 Claims, 10 Drawing Sheets

(51) Int. Cl.
  *G01J 5/02* (2022.01)
  *G06V 20/10* (2022.01)
  *H04N 23/11* (2023.01)
  *G01J 5/00* (2022.01)

(52) U.S. Cl.
  CPC .... *G06V 20/188* (2022.01); *G01J 2003/2826* (2013.01); *G01J 2005/0077* (2013.01); *G06T 2207/10036* (2013.01); *G06T 2207/10048* (2013.01); *G06T 2207/30188* (2013.01)

(56) References Cited

U.S. PATENT DOCUMENTS

| | | | |
|---|---|---|---|
| 6,211,906 B1 | 4/2001 | Sun | |
| 7,620,265 B1 * | 11/2009 | Wolff | G06T 5/50 |
| | | | 382/284 |
| 9,945,828 B1 | 4/2018 | Poling et al. | |
| 12,180,696 B1 * | 12/2024 | Salem | E04B 1/24 |
| 2007/0188650 A1 | 8/2007 | Kobayashi et al. | |
| 2016/0006951 A1 * | 1/2016 | Moghadam | G03B 35/02 |
| | | | 348/164 |
| 2016/0196653 A1 | 7/2016 | Grant et al. | |
| 2017/0308994 A1 | 10/2017 | Evers-Senne | |
| 2018/0003656 A1 | 1/2018 | Michini et al. | |
| 2018/0266886 A1 | 9/2018 | Frank et al. | |
| 2022/0038644 A1 * | 2/2022 | McAllister | G06V 20/194 |
| 2023/0162488 A1 * | 5/2023 | Boulanger | G06V 10/82 |
| | | | 382/157 |

FOREIGN PATENT DOCUMENTS

| | | |
|---|---|---|
| CN | 102506938 A | 6/2012 |
| CN | 103761732 A | 4/2014 |
| CN | 104237122 A | 12/2014 |
| DE | 102010005265 A1 | 7/2011 |
| EP | 2608532 A2 | 6/2013 |
| GB | 2547416 A | 8/2017 |

* cited by examiner

IMAGE SENSOR AND THERMAL CAMERA DEVICE, SYSTEM AND METHOD

BACKGROUND

Technical Field

The present disclosure is generally directed to generating and processing image streams captured by one or more thermal image sensors together with image streams captured by one or more spectral image sensors.

Description of the Related Art

Thermal imaging devices, such as Long-Wave Infrared (LWIR) imagers and other thermal cameras, may be used to capture thermal images of a target. The captured images may be used to estimate the temperature of the target object.

Spectral imaging devices, such as multispectral imaging devices, may be used to capture spectral images of a target. Images acquired by such spectral imaging devices may be utilized to measure or determine different characteristics of the target.

Irradiance sensing devices, such as photo sensors, may be configured to sense irradiance from a light source. The sensed irradiance may be used to process images, such as images received from thermal imaging devices and spectral imaging devices.

BRIEF SUMMARY

In an embodiment, a device comprises: thermal imaging circuitry, which, in operation, executes a sequence of thermal image capture cycles to capture a sequence of thermal images; spectral imaging circuitry, which, in operation, executes a sequence of spectral image capture cycles to capture a sequence of spectral images; and control circuitry, coupled to the thermal imaging circuitry and to the spectral imaging circuitry, wherein the control circuitry, in operation, synchronizes execution of spectral image capture cycles by the spectral imaging circuitry with execution of thermal image capture cycles by the thermal imaging circuitry.

In an embodiment, the device comprises one or more additional spectral imaging circuits, wherein the control circuitry, in operation, synchronizes execution of spectral image capture cycles by the one or more additional spectral imaging circuits with the execution of the thermal image capture cycles by the thermal imaging circuitry. In an embodiment, the spectral image circuitry and the one or more additional spectral image circuits have a common shutter. In an embodiment, the control circuitry, in operation, generates a digital surface model based on the sequence of spectral images. In an embodiment, the control circuitry, in operation, generates the digital surface model based on the sequence of thermal images.

In an embodiment, the control circuitry, in operation, generates a composite pixel map of an area of interest based on the digital surface model. In an embodiment, the control circuitry, in operation, identifies distressed plants based on the composite pixel map. In an embodiment, the control circuitry, in operation, estimates temperatures of pixels or groups of pixels in the composite pixel map. In an embodiment, the control circuitry, in operation, estimates pixel conditions based on the composite pixel map and the estimated temperatures. In an embodiment, the control circuitry, in operation, identifies distressed plants based on the composite pixel map and the estimated temperatures. In an embodiment, the control circuitry synchronizes a spectral image capture cycle with every ninth thermal image capture cycle. Other rates of synchronization are envisioned, such as every other thermal image capture cycle. Alternatively, the control circuitry may synchronize the shutter of the thermal image capture device and the spectral image capture device on every hundredth thermal image capture. The range of synchronized captures of thermal and spectral images can be a simultaneously shutter at every other thermal capture to every hundredth thermal capture. The cycle time can be selected based on the specific operation times of each of the thermal and spectral imaging devices. In an embodiment, the control circuitry, in operation, identifies conditions consistent with an irrigation leak based on the estimated pixel conditions. In an embodiment, the device is an aerial vehicle.

In an embodiment, a method comprises: executing, by a thermal imaging device, a sequence of thermal image capture cycles to capture a sequence of thermal images; synchronizing execution, by a spectral imaging device, of spectral image capture cycles to capture a sequence of spectral images with execution of thermal image capture cycles by the thermal imaging device; and generating a digital surface model of an area of interest based on the sequence of spectral images. In an embodiment, the method comprises synchronizing execution of spectral image capture cycles by a plurality of spectral imaging devices with the execution of the thermal image capture cycles by the thermal imaging circuitry. In an embodiment, the digital surface model is based on the sequence of thermal images. In an embodiment, the method comprises generating a composite pixel map of the area of interest based on the digital surface model. In an embodiment, the method comprises identifying distressed plants based on the composite pixel map. In an embodiment, the method comprises estimating temperatures of pixels or groups of pixels in the composite pixel map. In an embodiment, the method comprises estimating pixel conditions based on the composite pixel map and the estimated temperatures. In an embodiment, the method comprises identifying irrigation leaks based on the pixel occupancy map and the estimated temperatures.

In an embodiment, a device comprises: thermal imaging circuitry, which, in operation, executes a sequence of thermal image capture cycles to capture a sequence of thermal images; spectral imaging circuitry, which, in operation, executes a sequence of spectral image capture cycles to capture a sequence of spectral images; inertial motion sensing circuitry, which, in operation, generates data indicative of relative movement of the device; and control circuitry, coupled to the thermal imaging circuitry, to the spectral imaging circuitry, and to the inertial motion sensing circuitry, wherein the control circuitry, in operation: synchronizes execution of spectral image capture cycles by the spectral imaging circuitry with execution of thermal image capture cycles by the thermal imaging circuitry; and estimates a pose of a thermal image of the sequence of thermal images based on the data indicative of relative movement of the device. In an embodiment, the inertial motion sensing circuitry comprises an accelerometer. In an embodiment, the inertial motion sensing circuitry comprises a gyroscope. In an embodiment, the control circuitry, in operation, generates a digital surface model based on the sequence of spectral images. In an embodiment, the control circuitry, in operation, generates the digital surface model based on the sequence of thermal images. In an embodiment, the control circuitry, in operation, generates the digital surface model based on the estimated pose of the thermal image.

In an embodiment, a method comprises: executing, by a thermal imaging device, a sequence of thermal image capture cycles to capture a sequence of thermal images; synchronizing execution, by a spectral imaging device, of spectral image capture cycles to capture a sequence of spectral images with execution of thermal image capture cycles by the thermal imaging device; capturing inertial motion data; estimating a pose of a thermal image in the sequence of thermal images based on the captured inertial motion data; and generating a digital surface model of an area of interest based on the sequence of spectral images.

In an embodiment, a device comprises: thermal imaging circuitry, which, in operation, executes a sequence of thermal image capture cycles to capture a sequence of thermal images; spectral imaging circuitry, which, in operation, executes a sequence of spectral image capture cycles to capture a sequence of spectral images; irradiance sensing circuitry, which, in operation, senses irradiance data indicative of a background temperature; and control circuitry, coupled to the thermal imaging circuitry, to the spectral imaging circuitry, and to the irradiance sensing circuitry, wherein the control circuitry, in operation: synchronizes execution of spectral image capture cycles by the spectral imaging circuitry with execution of thermal image capture cycles by the thermal imaging circuitry; generates a digital surface model based on the sequence of spectral images; estimates an emissivity of a target; and estimates a temperature of a pixel of the digital surface model based on the sequence of thermal images, the irradiance data indicative of the background temperature, and the estimated emissivity of the target. In an embodiment, the irradiance sensing circuitry comprises a plurality of photo sensors.

In an embodiment, a method comprises: executing, by a thermal imaging device, a sequence of thermal image capture cycles to capture a sequence of thermal images; synchronizing execution, by a spectral imaging device, of spectral image capture cycles to capture a sequence of spectral images with execution of thermal image capture cycles by the thermal imaging device; sensing irradiance data indicative of a background temperature; generating a digital surface model based on the sequence of spectral images; estimates an emissivity of a target; and estimating a temperature of a pixel of the digital surface model based on the sequence of thermal images, the irradiance data indicative of the background temperature and the estimated emissivity of the target.

BRIEF DESCRIPTION OF THE SEVERAL VIEWS OF THE DRAWINGS

In the drawings, identical reference numbers identify similar elements unless the context indicates otherwise. The sizes and relative positions of elements in the drawings are not necessarily drawn to scale.

DETAILED DESCRIPTION

The present disclosure is directed to devices, systems and methods of generating and processing image streams captured by one or more thermal image sensors together with image streams captured by one or more spectral image sensors. The thermal image sensor is fixed with respect to the spectral image sensor. In addition, the thermal image sensor and the spectral image sensor are synchronized to capture images concurrently or simultaneously.

Figure 1:
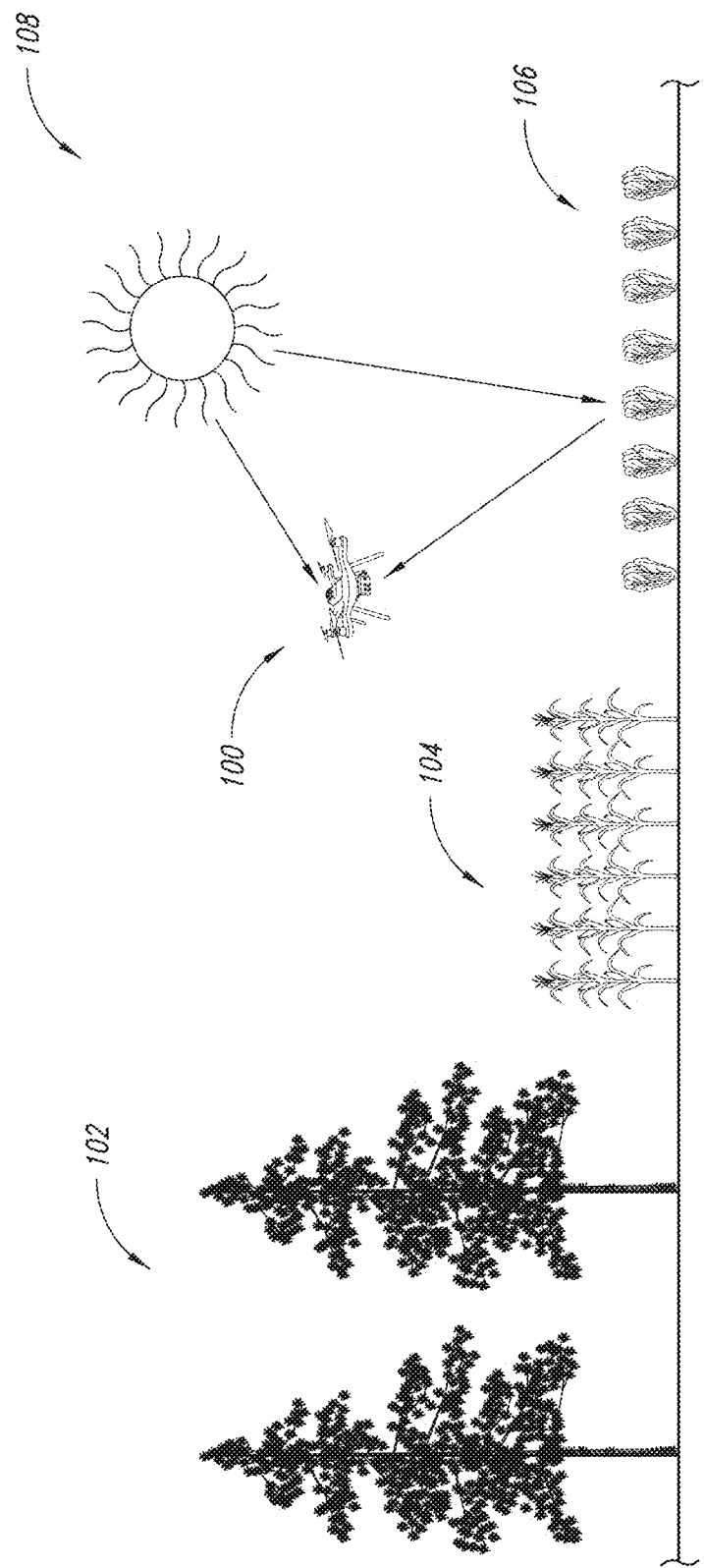
FIG. 1 illustrates an aerial vehicle to obtain thermal and multispectral images of a target, in accordance with one or more embodiments of the present disclosure.
Figure 2:
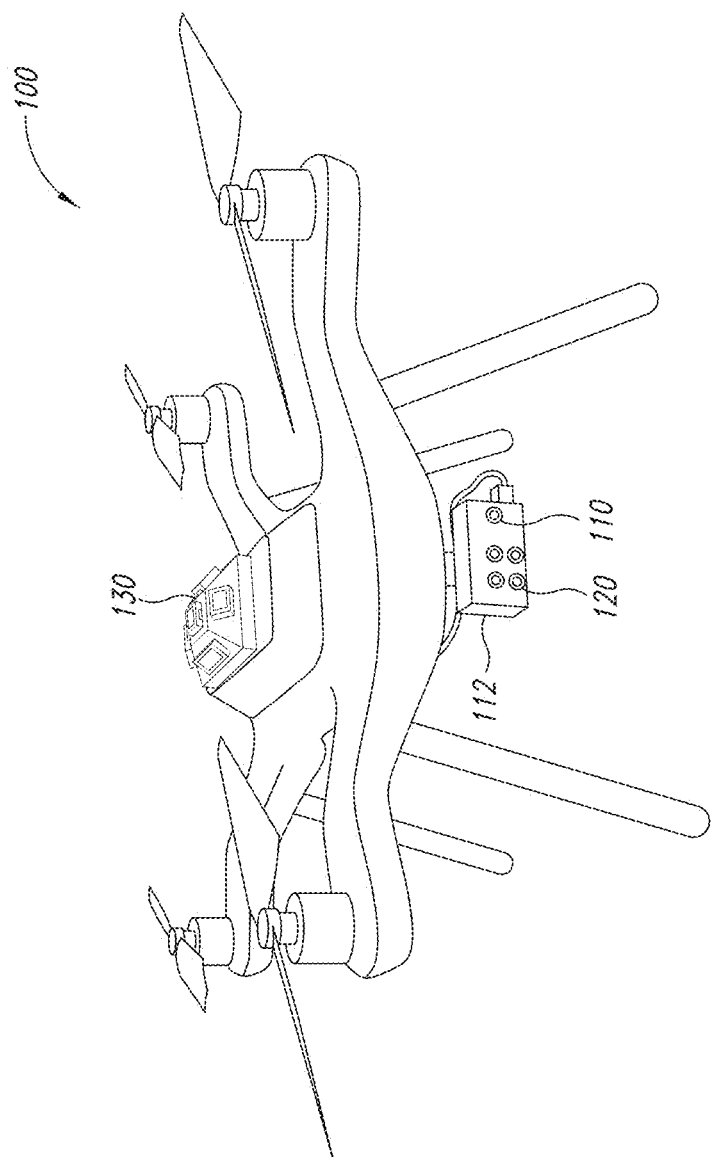
FIG. 2 illustrates details of an aerial vehicle in accordance with one or more embodiments of the present disclosure.

FIG. 1 illustrates an aerial vehicle 100 for simultaneously obtaining thermal and spectral images, for example, of a ground-based target, in accordance with one or more embodiments, and FIG. 2 illustrates further details of an embodiment of the aerial vehicle 100. Referring to FIGS. 1 and 2, the aerial vehicle 100 includes one or more thermal imaging devices 110, which, in operation, capture thermal images of a physical area or scene (e.g., a target) and one or more spectral imaging devices 120, which, in operation, capture spectral images of the physical area or scene (e.g., the target). As illustrated, the vehicle 100 also includes one or more irradiance sensing devices 130, which, in operation, sense irradiance levels.

The aerial vehicle 100 may be any type of aerial vehicle, including any rotary or fixed wing aerial vehicle, and may be an unmanned vehicle (as shown in FIG. 1) or manned aerial vehicle, such as an airplane or a drone. Additionally, the aerial vehicle 100 may be an autonomous vehicle, capable of autonomous flight (and autonomous acquisition of image and irradiance information), or may be a piloted vehicle (e.g., flown by a pilot in a manned vehicle, or by a remote pilot of an unmanned vehicle).

The imaged target (e.g., trees 102, crops 104, 106, a field of grass, a body of water or the like) receives irradiance from a light source, such as the sun 108. The target may be one or more distinct objects (e.g., a single tree, a building, a pond, etc.), an area or scene (e.g., a portion of a forest, a portion of a field of crops, a portion of a lake, etc.) or any other target for which the acquisition of an image may be desired. The number of thermal imaging devices or circuits 110 and the number of spectral imaging devices or circuits 120 may vary, for example, based on the type of targets or areas of interest. For example, in storm damage assessment applications (e.g., roof leaks), an aerial vehicle 100 having a single thermal imaging device 110 and a single spectral imaging device 120 may be employed, while in agricultural assessment applications, multiple thermal imaging devices 110 and spectral imaging devices 120 may be employed. It is envisioned that the systems and methods of the present application may be indoor such that ambient light is incandescent or LED.

The thermal imaging device 110 may be a free-running thermal imager such as a Long-Wave Infrared (LWIR) imager, capable of acquiring thermal images of a target, and may include multiple thermal imagers. Other thermal imaging devices may be employed, such as Short-Wave Infrared (SWIR) imagers, thermopiles, etc., and various combinations thereof.

Images acquired by the thermal imaging device 110 may be utilized to measure or determine different characteristics of the target, such as to estimate the temperature of a target object. The thermal imaging device 110 may be mounted to the aerial vehicle 100 and oriented in any manner as may be desired. For example, the thermal imaging device 110 may be mounted to a lower surface of the aerial vehicle 100 and positioned such that images of ground-based targets may be obtained. The thermal images may be RGB images.

The spectral imaging device 120 may be a multispectral imaging device capable of acquiring spectral images of a target, and may include multiple imagers, with each such imager being tuned for capturing particular wavelengths of light that is reflected by the target. The spectral imaging device 120 may be configured to capture reflected light in one or more of the ultraviolet, visible, near-infrared, and/or infrared regions of the electromagnetic spectrum. The spectral images may be RGB images.

Images acquired by such spectral imaging devices may be utilized to measure or determine different characteristics of the target, such as the chlorophyll content of a plant, an amount of leaf area per unit ground area, an amount or type of algae in a body of water, and the like. In one or more embodiments, the spectral imaging device 120 may be used to determine the reflectance of the imaged target.

The spectral imaging device 120 may be mounted to the aerial vehicle 100 and oriented in any manner as may be desired. For example, the imaging device 120 may be mounted to a lower surface of the aerial vehicle 100 and positioned such that images of ground-based targets may be obtained.

As illustrated, a sensor 112 houses the thermal imaging device 110 and the spectral imaging device 120. The sensor 112 is mounted to a lower surface of the aerial vehicle 100. The thermal imaging device 110 and the spectral imaging device 120 may acquire thermal and spectral images simultaneously. The sensor 112 includes a processor or circuitry that is coupled to the thermal imaging device 110 and to the spectral imaging device 120. The processor is configured to operate shutters of each of the thermal and spectral imaging devices in a manner to robustly capture thermal and spectral data such that the data can be processed and collated for a user to understand more about the environment they are evaluating with the vehicle 100.

The irradiance sensing device 130 may be mounted to an upper surface of the aerial device 100, and includes a plurality of photo sensors configured to simultaneously sense irradiance from a light source, such as the sun 108, at various different orientations with respect to the light source. The irradiance sensing device 130 is described in more detail with respect to FIG. 7 below.

Figure 3:
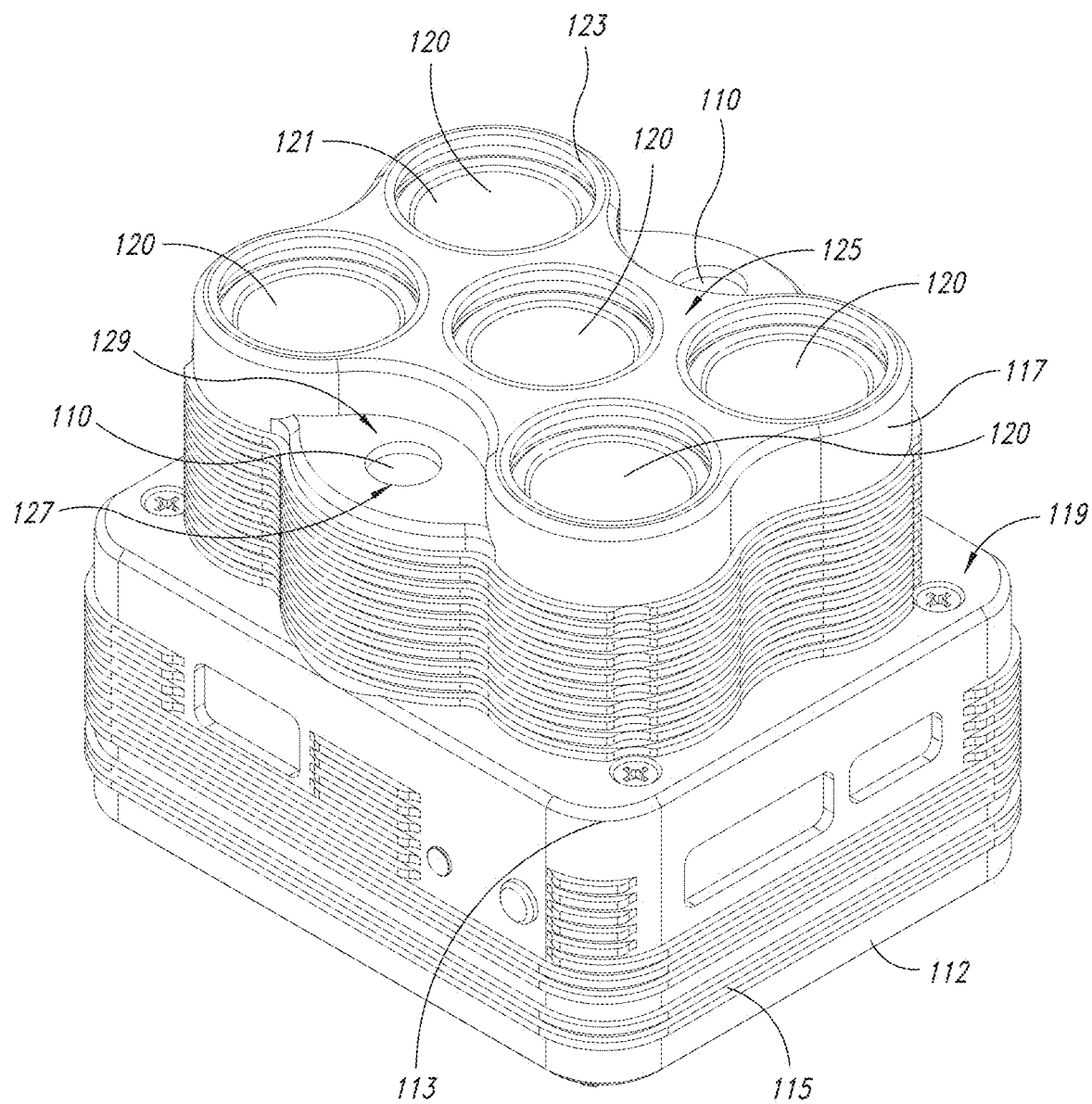
FIG. 3 is a perspective view of a sensor having thermal imaging and spectral imaging devices, in accordance with one or more embodiments of the present disclosure.

FIG. 3 shows a perspective view of an alternative embodiment of a sensor 112 having at least one thermal imaging device 110 and at least one spectral imaging device 120, in accordance with one or more embodiments of the present disclosure. As illustrated, the sensor 112 has two thermal imaging devices 110 and five spectral imaging devices 120.

The five spectral imaging devices may capture spectral images in different image bands (e.g., blue, green, red, red edge and near infrared bands). The thermal imaging devices 110 and the spectral imaging devices 120 as illustrated are rigidly positioned with respect to each other. In a typical sensor 112, the thermal imaging devices 110 may have a larger field of view and a lower resolution than the spectral imaging devices 120. For example, a thermal imaging device may have a resolution of 160 by 120 thermal pixels and a field of view of 57 degrees by 44 degrees, while a spectral imaging device may have a resolution 2064 by 1544 pixels and a field of view of 48 degrees by 37 degrees. Due to the higher resolution of the spectral images, it typically takes longer to write a captured spectral image to memory. Thus, the thermal imaging devices 110 in practice may have a faster operating cycle than the spectral imaging devices 120.

The sensor 112 includes a housing 113 that encloses various circuits, including a processor, a power supply, such as a battery, a transceiver or other communication means, such as a wire or wireless transmission circuitry. The housing 113 includes a base portion 115 and a lens portion 117 that extends away from a surface 119 of the base portion. The lens portion 117 includes 5 lenses 121 positioned in openings 123 though as surface 125 that is the outermost surface from the surface 119. Each lens is recessed into the opening such that a curvature of each lens is recessed from the surface 125. In other embodiments, the curvature of each lens or of some of the lenses may be equal to or extending past the surface 125.

Within the lens portion and coupled to the base portion are the spectral imaging chips or packages that are aligned with a respective lens 121. They are rigidly positioned within the housing 113. A first spectral imaging device is centrally positioned within the lens portion 117. Two spectral imaging devices are to the right of the centrally positioned spectral imaging device and two spectral imaging devices are to the left of the centrally positioned spectral imaging device. The centrally positioned spectral imaging device is also positioned between the first and second thermal imaging devices. These thermal imaging devices are also aligned with holes 127 in a surface 129. The surface 129 is recessed with respect to the surface 125. The surface 129 is between the surface 125 and the surface 119.

Figure 4:
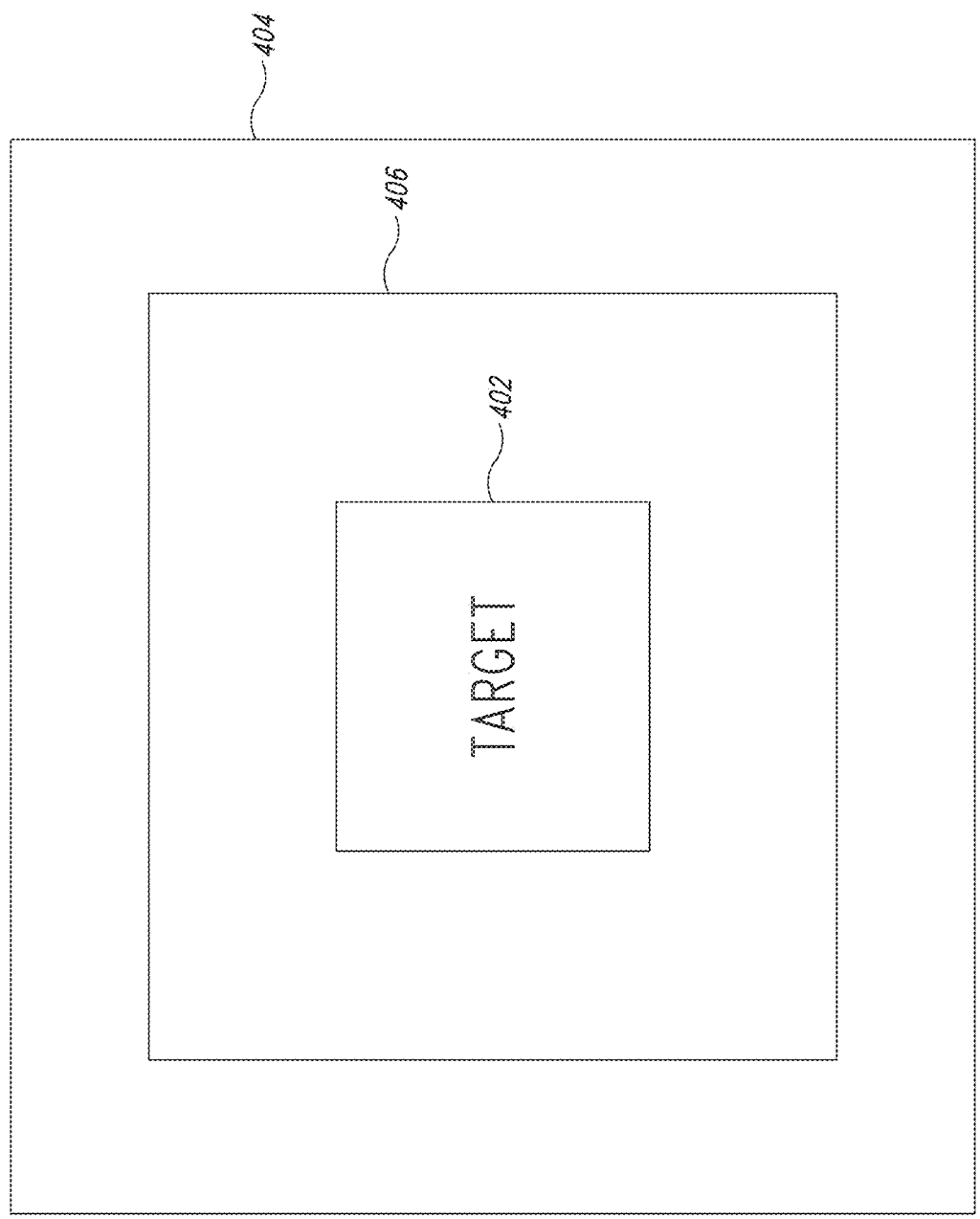
FIGS. 4 and 5 illustrate example images captured with a sensor, in accordance with one or more embodiments of the present disclosure.
Figure 5:
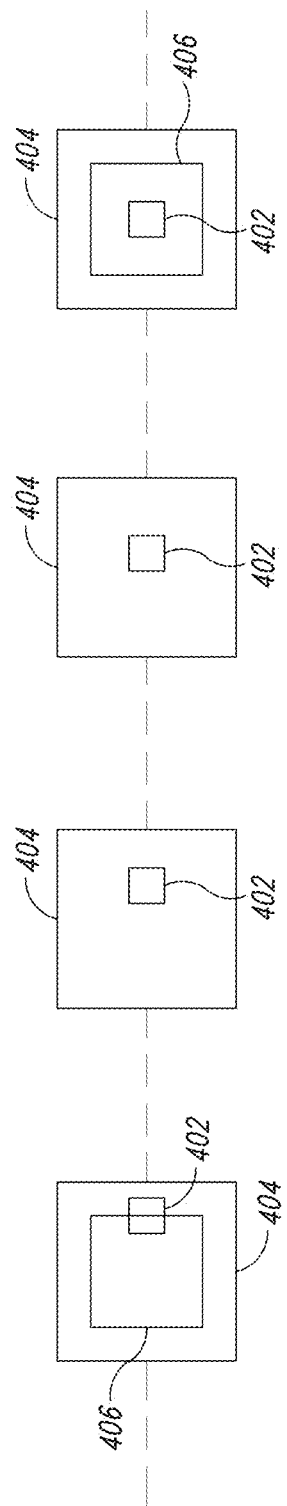

FIGS. 4 and 5 conceptually illustrate example images that may be captured with a sensor, such as the sensor 112 of FIG. 3, in accordance with one or more embodiments of the present disclosure. For ease of illustration, FIGS. 4 and 5 illustrate images captured using a single thermal imaging device 110 and from a single spectral imaging device 120 of the sensor 112. In practice, images may be captured by all of the thermal imaging devices 110 and spectral imaging devices 120 of the sensor 112. The thermal imaging device 110 captures thermal images 404, which include one or more targets 402, and the spectral imaging device captures spectral images 406, which include the target 402. A target may be a feature, such as an object or a point or feature of an object, an individual pixel (e.g., a thermal pixel, a spectral pixel), a group of pixels of a defined size (e.g., a four by four group of pixels), or a set of pixels associated with a feature, such as an object or a point of an object.

FIG. 4 illustrates a single thermal image 404 captured by the thermal imaging device 110 overlaid with a single spectral image 406 captured by the spectral imaging device 120. FIG. 5 illustrates a series of thermal images 404 and spectral images 406 captured by the thermal imaging device 110 and the spectral imaging device 120 as the sensor 112 moves by the target 402. As illustrated, the thermal imaging device 110 has a fixed field of view which is broader than the fixed field of view of the spectral imaging device 120.

As the thermal imaging device 110 in practice has a faster image capture cycle time (typically due to the lower resolution), more thermal images 404 are captured by the thermal imaging device 110 than spectral images 406 are captured by the spectral imaging device 120 as shown in FIG. 5. In other words, the thermal images 404 have a higher spatial sampling frequency than the spectral images 406, in addition to being captured at different wavelengths. As illustrated, four thermal images 404 are captured by the thermal imaging device 110 and two spectral images are captured by the spectral imaging device 120 during a pass over the target 402 by the sensor 112. In practice, a thermal imaging device 110 may be able to capture eight or more thermal images 404 in the same time period in which the spectral imaging device 120 captures a single spectral image 406.

Figure 6:
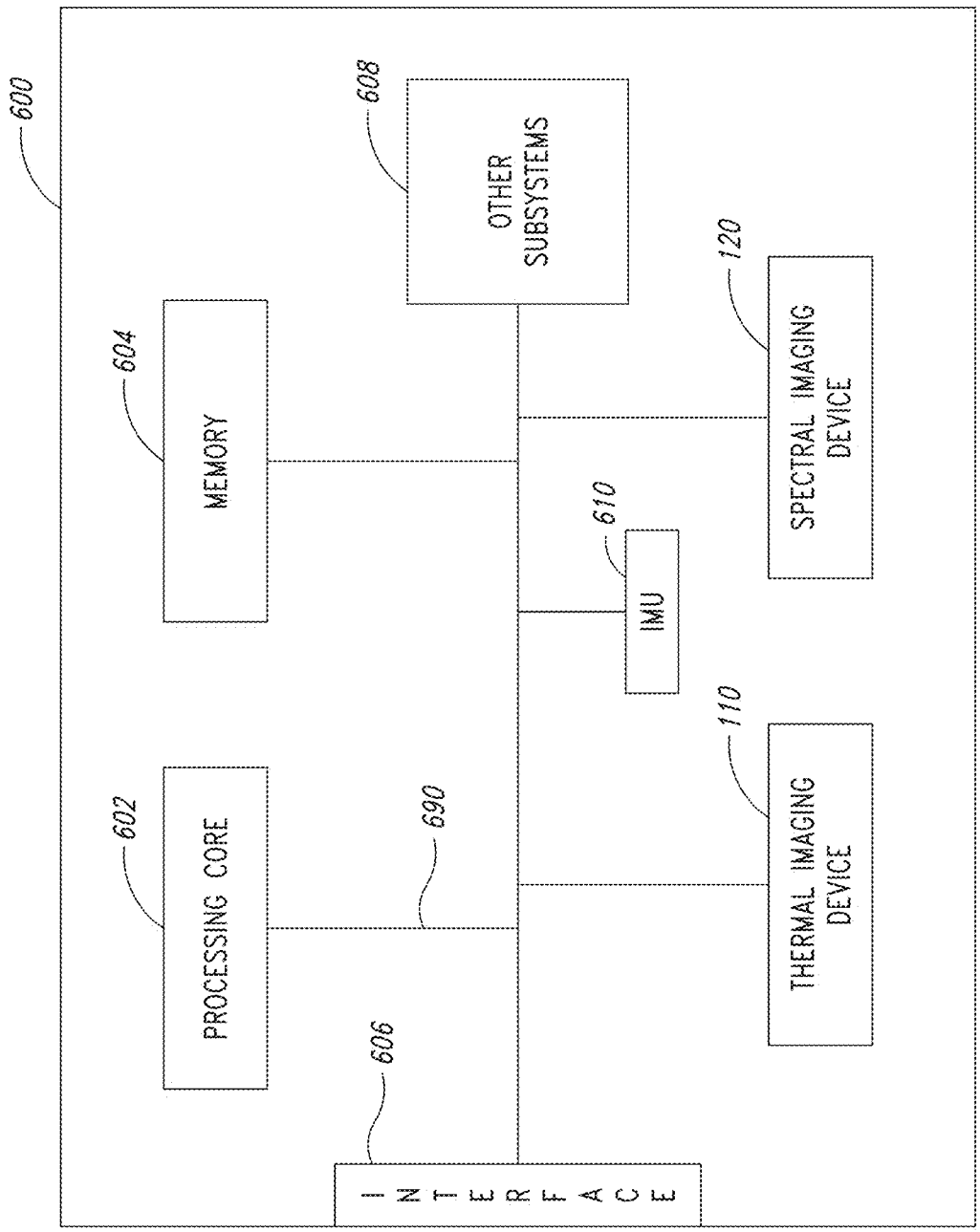
FIG. 6 is a functional block diagram of a sensor or camera having thermal imaging and spectral imaging devices, in accordance with one or more embodiments of the present disclosure.

FIG. 6 is a functional block diagram of an embodiment of a sensor 600, which may be employed, for example, as the sensor 112 of FIGS. 1-3, to capture images of one or more targets. The sensor 600 includes one or more thermal imaging devices 110, which, in operation, capture thermal images, and one or more spectral imaging devices 120, which, in operation, capture spectral images. As illustrated, the system 600 comprises one or more processing cores or processors 602, and one or more memories 604, which may be used in operation to implement the functionality of the sensor 600 (e.g., to control the thermal imaging devices 110 and the spectral imaging devices 120, to store and process thermal image data and spectral image date, etc.), for example, by executing instructions stored in the memory. The system 600 as illustrated also comprises one or more bus systems 606, and may include additional circuitry 608, such as power supplies, etc., which are omitted for ease of illustration. The system also includes one or more inertial measurement units (IMU) 610, such as a gyroscope or accelerometer, which may, in operation, generate position change information as the aerial vehicle 100 captures images of a target.

Embodiments of the sensor 600 may comprise more or fewer circuits than illustrated, and circuits may be combined and separated into additional circuits in various manners. For example, some embodiments of the sensor 600 may incorporate an irradiance sensing device (see irradiance sensing device 130 of FIG. 1). In some embodiments, the sensor may be configured to couple to an external irradiance sensing device. Some embodiments may include telecommunication circuitry (e.g., wifi or cellular), or include such functionality in the interface 606.

In operation, a thermal image 404 generated by the thermal imaging device 110 of the sensor 112 may be used to estimate the temperature of individual pixels of a target. By combining multiple thermal images 404 and further considering the spectral images of the target 406 generated by one or more of the spectral imaging devices 120, an increase in the spatial resolution of the temperature estimates may be obtained. The spectral images 406 may be used, for example, to estimate an emissivity of the target, and the emissivity estimate may be used with the measured temperature information from the thermal images 404 to estimate a temperature of the target. Emissivity is a property of a material of a surface and is a ratio of the energy radiated from a materials surface to that of a blackbody. A perfect emitter (blackbody) has an emissivity of 1 and emits longwave radiation that is equal to its temperature. A perfect thermal mirror has an emissivity of 0. Other materials have an emissivity between 0 and 1. A material with an emissivity less than 1 emits radiation proportional to its temperature. Glass is opaque to longwave radiation, and reflects more than it emits. To estimate the temperature, the emissivity is estimated.

A spectral image 406 may be used to identify target objects and to detect conditions of the target object, such as whether a plant is under stress, whether pipes under a field are leaking, etc. A 3-D digital surface model (DSM) may be generated using multiple spectral images 406 captured as the aerial vehicle 100 moves over the target. Combining spectral image data from a spectral image 406 with thermal image data from one or more thermal images 404 may facilitate generating more accurate estimates of the conditions of a target. The thermal images 404 may be used in combination with the spectral images 406 to generate the DSM. The DSM is a representation of the surface of the earth or environment which is being imaged. The DSM represents elevation differences and reflectance of the objects in the environment. Temperature information of the objects and the environment are incorporated in the DSM based on the thermal images.

Also, data from the irradiance sensing device 130 may be used to estimate the background temperature (e.g., the temperature of the sky). The estimated background temperature information may be used to adjust or correct the measured temperatures of the pixels of the target, increasing the accuracy of temperature estimates and of any condition data based in part on temperature estimates.

Figure 7:
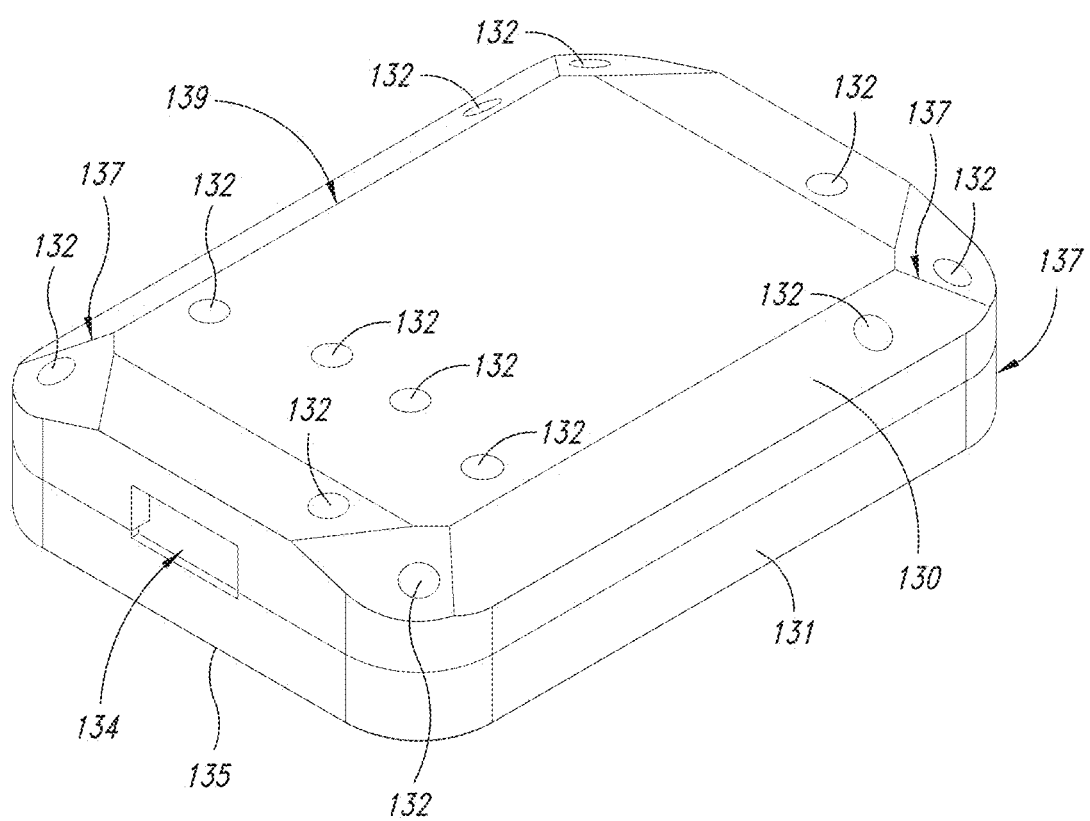
FIG. 7 is a perspective view of an irradiance sensing device, in accordance with one or more embodiments of the present disclosure.

FIG. 7 shows a perspective view of an irradiance sensing device 130, in accordance with one or more embodiments of the present disclosure. The irradiance sensing device includes a plurality of photo sensors 132 configured to simultaneously sense irradiance from a light source, such as the sun (see FIG. 1), at various different orientations with respect to the light source. As illustrated, the irradiance sensing device 130 includes an interface 134, which may, in operation, be coupled to a processing device, such as the processing core 602 of sensor 600 via the interface 606 of FIG. 6.

The photo sensors 132 may be multi-spectral downwelling light sensors. Data or images from the photo sensors 132 may be used to estimate the temperature distribution of the sky during aerial thermography. The photo sensors 132 may measure the angle and diffusivity ratio of light paths. A model of the hemispherical incoming irradiance may be generated based on the measured information and used to estimate a temperature of the sky.

The photo sensors measure solar irradiance in radiometric remote sensing applications. Irradiance from a light source, such as the sun, may be simultaneously sensed by a plurality of photo sensors arranged at differing orientations on an irradiance sensing device. Components of the irradiance, such as the direct and scattered components and the incidence angle, may thus be determined, and utilized to compensate or normalize images of a target that are acquired at the same time by an imaging device.

By simultaneously sensing irradiance by multiple photo sensors having different orientations, it is possible to determine particular characteristics of the light source, such as the direct and scattered components of solar irradiance, as well as an angle of incidence a of the solar irradiance. Moreover, the irradiance sensing device may sense irradiance at the same time as images are acquired by the imaging device, which enables normalization or compensation of the acquired images to account for variations in received irradiance by the imaged target. For example, an image of a target acquired by the imaging device 100 on a cloudy day can be correlated to an image acquired of the same target on a cloudless day, by accounting for the differences in the irradiance sensed by the irradiance sensing device 130 at the time of acquiring each image (thermal and/or spectral).

The irradiance sensing device 130 includes a plurality of irradiance sensing surfaces arranged at different orientations and photo sensors configured to receive and sense varying amounts or components (e.g., direct and scattered components) of irradiance from a light source such as the sun. The irradiance sensing device 130 can be attached to the aerial vehicle and communicatively coupled to the thermal and spectral imaging devices.

With reference to FIG. 7, the irradiance sensing device 130 includes a housing 131 which forms outer surfaces of the device 130. In some embodiments, the housing 131 may include two or more pieces that are securable to one another by any suitable elements, including, for example, by one or more of a fastener, adhesive material, hinges, or the like. In some embodiments the housing 131 includes a top enclosure 133 and a bottom enclosure 135.

The top enclosure 133 includes a plurality of inclined surfaces 137 which extend in different orientations between respective edges and an upper surface 139 of the top enclosure 133. A plurality of irradiance sensing openings 413 extend through the inclined surfaces 137 and/or the upper surface 139. In some embodiments, each of the inclined surfaces 137 and the upper surface 139 includes at least one irradiance sensing opening aligned with one of the photo sensors 132.

The plurality of photo sensors 132 is arranged on an internal board, which may be a mounting structure for mounting the photo sensors, and in some embodiments carries various electronic circuitry, components, or the like included in the irradiance sensing device 130.

Light pipes are positioned in the irradiance sensing openings and aligned with each photo sensor. The light pipes may be any physical structure capable of transmitting or distributing received irradiance from outside of the housing 131 into an interior of the housing 131, and more particularly, toward each of the photo sensors 132. The light pipes may have a hollow structure or a solid structure. In some embodiments, the light pipes are not included.

The photo sensors 132 may be configured to sense irradiance having various different wavelengths. For example, in one or more embodiments, the photo sensors includes one or more broadband photo sensors that sense ambient light or irradiance and one or spectral sensors that sense light having specific wavelengths or ranges of wavelengths across the electromagnetic spectrum. In some embodiments, broadband photo sensors are configured to sense light through the irradiance sensing openings of the inclined surfaces 137, while spectral sensors are configured to sense light through the irradiance sensing openings on the upper surface 139 of the top enclosure 133.

Various electronic circuitry (such as one or more application specific integrated circuits, computer-readable memory and the like) for processing and/or storing received signals (e.g., signals indicative of the sensed irradiance), may be attached to the internal board.

Each of the photo sensors 132 may be communicatively coupled to a processor (e.g., wirelessly coupled, or coupled by one or more electrical wires or cables) and, during operation, may communicate signals (e.g., one or more signals indicative of the sensed irradiance) to or from the processor. The processor may be configured to perform any of the functions described herein, including, for example, determining directed and scattered components of sensed irradiance, receiving acquired images, determining the reflectance of a target object based on determined direct and scattered components of sensed irradiance and an acquired image, storing information or causing information to be stored, correlating information, determining orientation of the irradiance sensing device 130, navigational functions, and so on.

In some embodiments, the present disclosure provides a device including a structure, and a plurality of photo sensors coupled to the structure. The photo sensors have different sensing orientations with respect to one another, and each of the photo sensors, in use, receives irradiance at a respective one of the plurality of sensing orientations. The different sensing orientations include at least five different sensing orientations. In some embodiments, the photo sensors have sensing surfaces that are arranged at the different sensing orientations. In some embodiments, a housing has a plurality of surfaces that have the different sensing orientations, and the photo sensors receive light incident on the surfaces. In some embodiments, the housing may have a hemispherical or spherical shape, with light being incident at a plurality of different sensing orientations on the housing, and the plurality of photo sensors receive light incident on different portions of the hemispherical or spherical housing.

The sensing orientations of the photo sensors may be different from one another in terms of angle or position with respect to any reference point. For example, the sensing orientations may have different angles with respect to a reference point, which may be measured, for example, from a center of the structure to which the photo sensors are attached. Each of the photo sensors may be configured to receive light incident at a particular surface area or region (e.g., at a surface area of the openings in the top enclosure 133 of the device 130). The amount of data generated by the thermal image sensors 110, the spectral image sensors 120, and the optional irradiance sensing device 130, may be quite substantial, and the processing, memory and power requirements associated with turning such a large of volume of data into a useful output (e.g., images of a target showing estimated temperatures of the target or portions thereof, images showing estimated conditions of a target, etc.) may similarly be quite substantial. The processing may be complicated by the differences in resolution between the thermal images and the spectral images, and the free-running of the thermal imaging devices.

One way to reduce the processing overhead is to discard most of the thermal images 404 generated by the thermal imaging device 110. For example, for each capturing of a spectral image 406, one thermal image 404 may be captured, and the rest of the thermal images 404 discarded. With reference to FIGS. 5 and 6, only the thermal images 404 captured at the same time as a spectral image 406 may be saved to memory 604. This reduces the memory requirements of the sensor 112, and may reduce the processing requirements associated with turning the data into a useful output. However, resolution of the thermal information is reduced.

Figure 8:
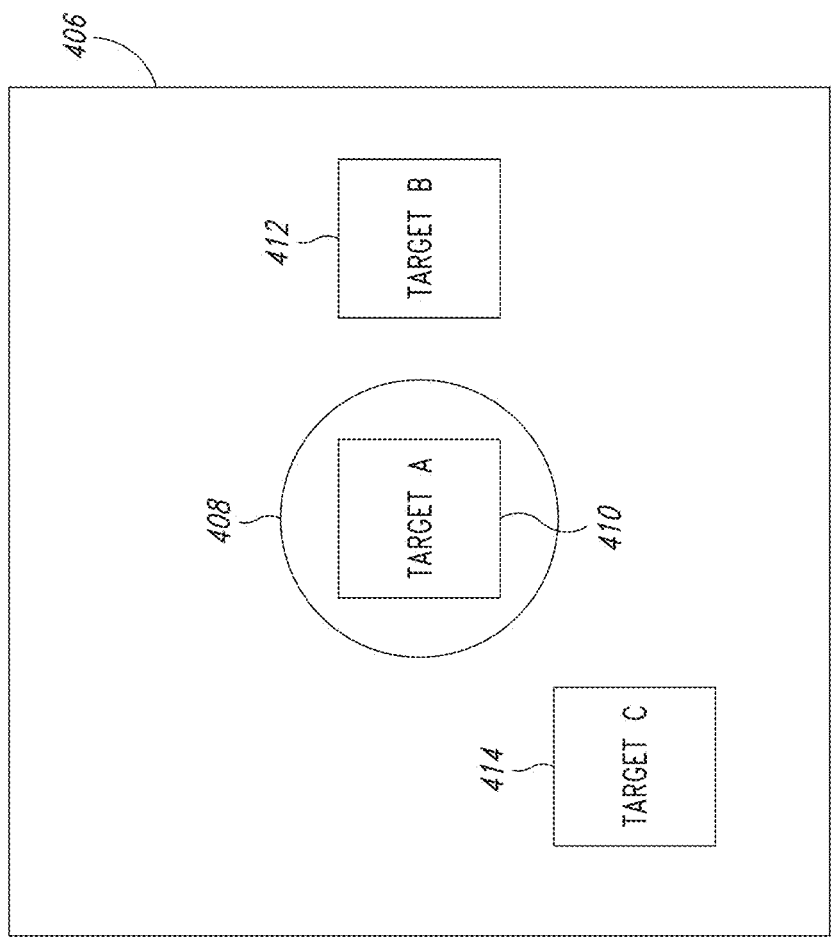
FIG. 8 illustrates an area within a spectral image captured by a spectral imaging device, in accordance with one or more embodiments of the present disclosure.

Another way to reduce the processing overhead is to limit the amount of information from the spectral images 406 that is saved and used to process the images (e.g., the amount of information used to generate the DSM). In the spectral images 406, only data from a central portion of the image 406 may be saved on the assumption that data in this portion of the image is the most useful. FIG. 8 illustrates this concept. The data within area 408 of the image 406 may be saved, and the data outside of area 408 may be discarded.

The size of the area 408 may be determined based on the Nyquist theorem. Saving only the best part of the data reduces memory requirements and may also decrease the spectral image capture cycle time. Thus, in the spectral image 406 of FIG. 8, data for target A 410 may be saved. However, data for target B 412 and data for target C 414 would be lost, which may reduce the accuracy of the DSM and the resolution of any useable output information, such as maps of target conditions. When all or more of the spectral image data than the data within area 408 is stored and used to generate the DSM, oversampling of targets is facilitated, which results in higher resolution images due to the spatial overlap in the spectral images. For example, data related to target B 412 and target C 414 is available from more of the spectral images.

Due to the free-wheeling of the thermal imaging device 110, thermal images 404 captured by one or more of the thermal imaging devices 110 are not synchronized with spectral images 406 captured by one or more of the spectral imaging devices 120. This increases the complexity of generating the DSM when thermal image data is combined with spectral image data.

To avoid this increase complexity, capturing of spectral images 406 by a spectral imaging device 120 may be synchronized to the capturing of thermal images by a thermal imaging device 110. This may facilitate capturing all of the thermal images and using more of the data of the spectral images, which in turn facilitates oversampling for both the spectral image and thermal image modeling. The synchronizing may, for example, be based on the capture cycle time of the spectral imaging device 120 and the capture cycle time of thermal imaging device 110. Based on the spectral and thermal image capture cycles, a number of cycles n of the thermal imaging device 110 may be determined, and capturing of an image by the spectral imaging device may be triggered every n cycle of the thermal imaging device. A spectral image capturing device 120 may capture an image frame every second, and a thermal image capture device 110 may capture 9 images a second. Thus, in such a case n may be set at 9.

When a plurality of spectral imaging devices 120 are synchronized to a thermal imaging device 110, an image capture cycle time of the slowest of the spectral imaging devices 120 may be used to determine the number of cycles n of the thermal imaging device 110 used to trigger capturing of spectral images 406 by the plurality of spectral imaging devices 120. To facilitate synchronizing of the spectral images thermal to each other and to the thermal image 404 captured by cycle n of the thermal imaging device 110, a common shutter may be employed by the plurality of spectral imaging devices 120, or the spectral imaging devices 120 may employ fast shutters. This facilitates the spectral image sensors having an overlapping recovery time. The common shutter may be facilitated by the processing core 602, controlling the timing of each sensor in the array or thermal and spectral imaging devices.

When one or more spectral imaging devices 120 are synchronized to a plurality of thermal imaging devices 110, an image capture cycle time of the slowest of the thermal imaging devices 110 may be used to determine the number of cycles n of the thermal imaging device 110 used to trigger capturing of spectral images 406 by the one or more spectral imaging devices 120. The thermal imaging devices 110 may be synchronized to each other, and a common thermal image cycle time may be used to determine the number of cycles n, etc.

Synchronizing capturing of spectral images 406 by one or more of the spectral imaging devices 120 with the capturing of thermal images 404 by the one or more thermal imaging devices 110 facilitates reducing the complexity of generating the DSM and using more data (such as all of the thermal images 404 and all or more of the data in the spectral images 406) to generate the DSM. Thus, synchronizing the capturing of spectral images with the capturing of thermal images facilitates oversampling of targets by facilitating the ability to use more of the spectral image data and the ability to use more thermal images, and may also facilitate generating the DSM using processing resources of the aerial vehicle (e.g., processing core 602 and memory 604 of sensor 112), instead of sending the data to a remote server to generate the DSM, due to faster processing. The increased in accuracy of the modeling facilitates reducing noise in the signal as well as providing higher resolution and clearer measurement results. There may be some tradeoff in reducing noise and providing clearer results in the DSM generation.

Figure 9:
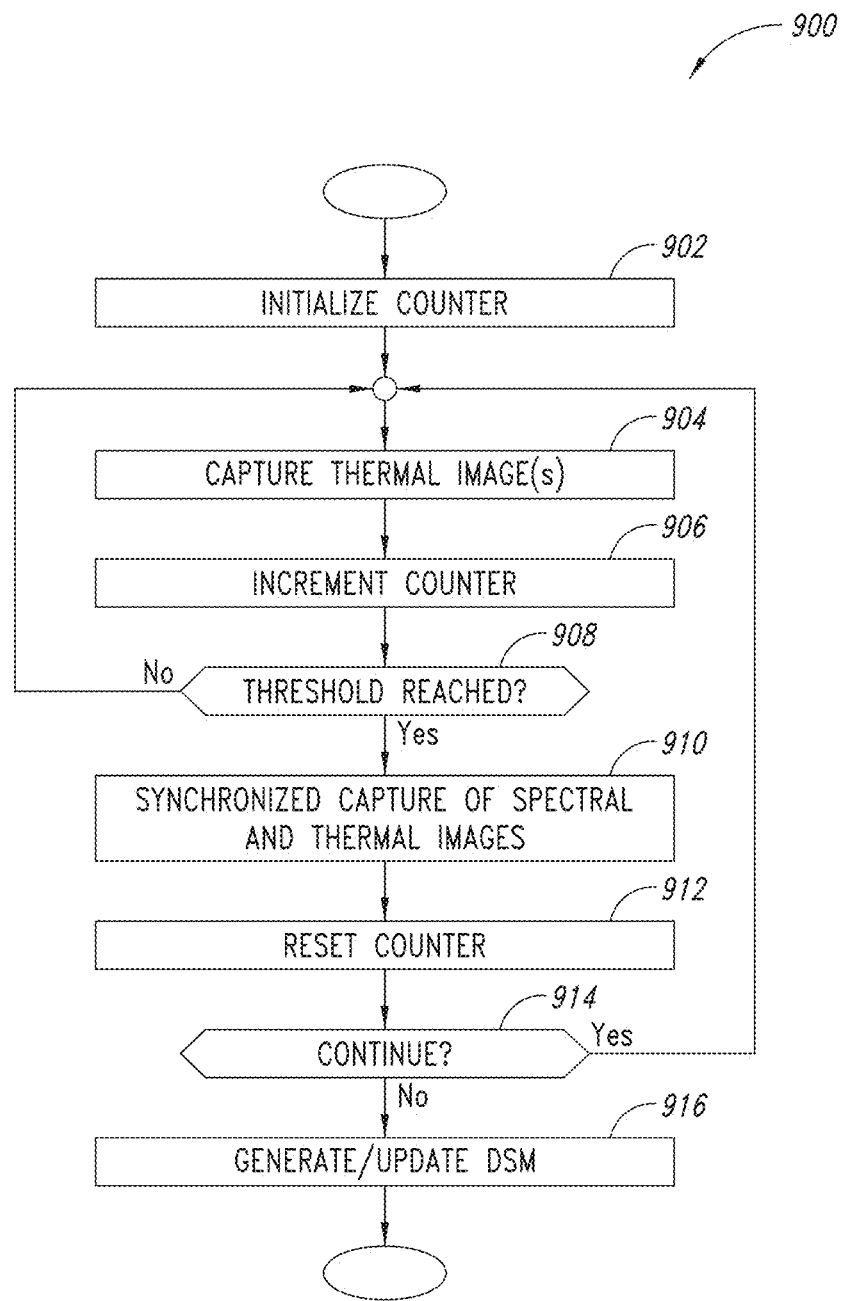
FIG. 9 is a flow chart illustrating one example process of generating capturing synchronized thermal and spectral images, and using the images to generate a digital surface model of a target area, in accordance with one or more embodiments of the present disclosure.

FIG. 9 is a flow chart illustrating one example process 900 of generating and capturing synchronized thermal and spectral images, and using the images to generate a digital surface model of a target area, such as a field. The process 900 may be performed, for example, by the aerial vehicle 100 of FIG. 1, or the sensor 112 of FIGS. 1-3 and 6.

At 902, the process 900 initializes one or more control variables or devices, such as a counter, the process 900 proceeds from 902 to 904. At 904, the process 900 executes a thermal image capture cycle, capturing a thermal image using a thermal imaging device such as the thermal imaging device 110 of FIG. 6. In some embodiments, additional thermal images may be captured during the thermal image capture cycle of 904 using additional thermal imaging devices. The capturing of the thermal images in the thermal image capture cycle at 904 may be synchronized. The process 900 proceeds from 904 to 906, where the control variables or the counter are updated or incremented to reflect occurrence of a thermal image capture cycle at 904. The process proceeds from 906 to 908.

At 908, the process 900 determines whether the next capture cycle of one or more thermal images should be synchronized with a capture cycle of one or more spectral images. As illustrated, this is done by determining whether a threshold number of thermal image capture cycles has been reached, for example by comparing a value of a counter to a threshold (e.g., n−1). When it is determined at 908 that the next capture cycle of one or more thermal images should be synchronized with a capture cycle of one or more spectral images, the process 900 proceeds to 910. When it is not determined at 908 that the next capture cycle of one or more thermal images should be synchronized with a capture cycle of one or more spectral images, the process 900 returns to 904 to execute another thermal image capture cycle.

At 910, the process synchronizes execution of a thermal image capture cycle with execution of a spectral image capture cycle. The capturing of one or more thermal image(s) using corresponding thermal imaging device(s) is synchronized with the capturing of one or more spectral image(s) by one or more spectral imaging device(s). This may be done, for example, by triggering a shutter or shutters of the one or more spectral imaging device at the same time as, or within a threshold period of time of the triggering of the thermal image capture cycle. The process 900 proceeds from 910 to 912, where the control variable or counter are reset. The process 900 proceeds from 912 to 914.

At 914, the process 900 determines whether to continue gathering image data. This process 900 may determine whether to continue gather image data based on control signals, threshold periods of time, buffer statuses, determined acquisition schedules, etc. When it is determined at 914 to continue gathering image data, the process 900 returns to 904. When it is not determined at 914 to continue gathering image data, the process 900 proceeds from 914 to 916.

At 916, the process 900 generates a DSM using the synchronized thermal and spectral images captured by the thermal and spectral imaging devices, such as imaging devices of the sensor 112 of FIG. 6. The DSM may be generated, for example, using the sensor 112 of FIGS. 1-3 and 6, the aerial vehicle 100 (e.g., a processing core of the aerial vehicle 100 separate from the sensor 112), by a remote server (not shown), and various combinations thereof. With reference to FIGS. 1-3 and 6, the synchronized images are captured as the aerial vehicle 100 is flown above an area of interest. The multiple images are captured from multiple angles.

The DSM is generated from high-resolution features contained in synchronized multispectral imagery. Photogrammetry techniques may be used to extract geometric information from the spectral images to identify the features. Techniques may be employed to account for lens distortions and alignment of the images using, for example, calibration information, feature detection, etc. Using the digital surface models and pose estimates from the multispectral images, and a prior or a posteriori relative angular information, the pose of the synchronized thermal imager 110 which captures thermal images at the same time may be estimated. This facilitates using the thermal images with a lower spatial sampling frequency to refine the DSM. The DSM, pose, and camera thermal model information may be used to estimate the temperature of each point on the digital surface model, at a higher resolution than resolution of the thermal pixels of the thermal imager. The radiometric response of each pixel in the imagery may be used to model the emissivity of the object under the pixel. The emissivity information may be used to calibrate each aligned thermal pixel to retrieve a temperature estimate of the surface temperature at that point. For example, the temperature estimate may be retrieved from a look up table.

Embodiments of the process 900 of FIG. 9 may include more acts than illustrated, may include fewer acts than illustrated, may separate illustrated acts into multiple acts, may combine illustrated acts into fewer acts, and may perform illustrated acts in various orders, which may include performing illustrated acts in parallel or using an iterative process. For example, in an embodiment of the process 900 a parallel process may be employed to simultaneously generate or update the DSM or composite output pixel maps while image capture cycles are being executed. In another example, generating the DSM may be an iterative process, in which images are reprocessed based on the DSM, and the DSM is updated based on the reprocessed images. In another example, the DSM may be generated in a remote server after the aerial vehicle has landed and the stored data has been transferred to the remote server for processing. In some embodiments, the DSM will be generated on the aerial vehicle and in other embodiments, the DSM will be generated after the flight on a separate processing device from the aerial vehicle.

In some embodiments, the composite pixel map may be based on data from the thermal and spectral images. For example, the spectral images may be used to create the DSM and estimate the emissivity of the pixels. Then the thermal information may provide the underlying value of the pixels for the composite pixel map.

In another example, the process 900 may be modified to capture background irradiance data using one or more irradiance sensing devices, such as the irradiance sensing device 130 of FIGS. 1 and 7. The capturing of irradiance data may be synchronized, for example, with each thermal image capture cycle, with each synchronized thermal and spectral image capture cycle, etc. A downwelling light sensor measures both the angle and diffusivity ratio of light paths, and a model of the hemispherical incoming irradiance derived are used to estimate the temperature of the sky. The estimated temperature of the sky may be used to correct the surface temperatures measurements using the emissivity, sky temperature, and measured pixel temperature. Measuring the irradiance of the sky facilitates a more accurate estimation of the temperature because it provides an indication of what portion of the radiation emitted by a surface is reflected, and thus allows for a better estimate of the material of the surface. The temperature of the sky can be subtracted from the measured temperature. For example, the emissivity of a tin roof can be estimated with a reflective curve, and a lookup table based on the relationship of reflectance to emissivity plus the temperature of the sky may be used to estimate the temperature. An estimate of the emissivity may be corrected based on the temperature of the sky, and then the thermal information may be corrected. This may be done on a pixel by pixel basis. Drones are closer to the ground than satellites and have bigger pixels than spectral images, which may further facilitate providing more accurate temperatures projected on the DSM.

In another example, the process 900 may be modified to capture inertial motion data using one or more IMUs, such as the IMU 610 of FIG. 6, and to use the inertial motion data to estimate the pose of images captured by the sensor, such as thermal images captured by the thermal imaging devices 110 of FIG. 6. The capturing of inertial motion data may be synchronized, for example, with each thermal image capture cycle, with each synchronized thermal and spectral image capture cycle, etc. The pose of each sequential thermal image captured by a thermal camera may be estimated by using the derived pose of synchronized captures from a visible camera. When the IMU includes a gyroscope the gyroscope may provide change in angle information, which may be integrated over a set of adjacent images. When the IMU includes accelerometer, the accelerometer may provide change in position information, which may typically not be integrated over adjacent images. The IMU data may be used to determine inter-frame pose change, and photogrammetry or image matching may be used to determine the pose changes and absolute pose of the visible imagery.

Figure 10:
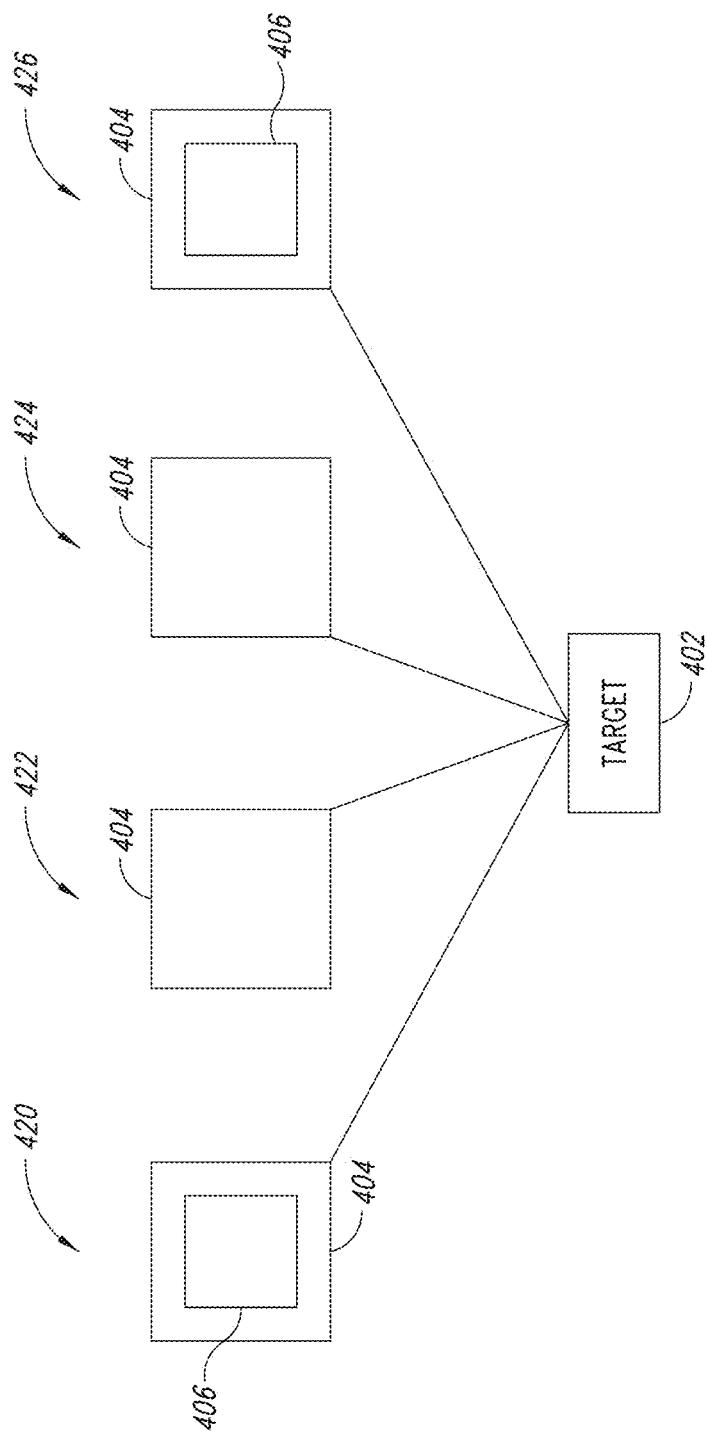
FIG. 10 illustrates example image capture cycles in accordance with one or more embodiments of the present disclosure.

With reference to FIG. 10, a synchronized image capture cycle 420 captures a spectral image 406 of a target synchronized with the capturing of a thermal image 404 of the target. Subsequent image capture cycles 422 and 424 capture respective thermal images 404 of the target, then synchronized image capture cycle 426 captures a spectral image 406 of the target synchronized with a thermal image 404 of the target. The pose (position and orientation) of the target 402 or point on the target 402 with respect to the thermal imaging devices 110 when image capture cycles 422 and 424 are executed may be estimated based on the IMU data and the pose estimates for image capture cycle 420. In an embodiment, the estimated poses at cycles 422 and 424 may also be based on the pose estimates for cycle 426. In an embodiment, other position information may also be considered, such as GPS information. In an embodiment, the thermal image data of images in a sequence of thermal images may be applied to estimate the pose of images captured at image capture cycles 422 and 424 before consideration of the spectral image data due to the lower resolution of the thermal images. Then spectral image data (oversampled) may be applied if further refinement of the estimated pose is desired. There may be some tradeoff in reducing the noise in measurements and improving the signal resolution in the estimated pose.

The DSM, data gathered by the sensor (e.g., the spectral images, the thermal images, any irradiance data, any accelerometer data, etc.), external or known data (e.g., GPS data, flight paths, etc.), may be used to characterize pixels of a composite output map generated based on the DSM. Captured images are projected onto the DSM based on camera position information. The information for a single point is projected from multiple angles by the multiple images. A pixel of the output map may be characterized, for example, as soil, shadow, plants, etc. The output pixel map may be used, for example, together with temperature information to identify issues which may need to be addressed.

For example, using the classified pixels of the output map, areas where the soil temperature or shadow temperature is statistically different and lower than the surrounding soil or shadowed areas may indicate areas where irrigation leaks are occurring. In another example, high resolution spectral images and temperature information may be used to identify distressed plants, such as grape vines in a field. For example, the human eye can detect stress 14 days after a plant experiences the stress. In an embodiment, high resolution spectral images using oversampling may detect plant stress within 5-6 days of the stress occurring. When combined with thermal mapping, the detection time frame may be reduced even further. In an embodiment, the oversampled thermal mapping can measure a 0.5 degrees Celsius change in temperature.

Some embodiments may take the form of or comprise computer program products. For example, according to one embodiment there is provided a computer readable medium comprising a computer program adapted to perform one or more of the methods or functions described above. The medium may be a physical storage medium, such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the methods and/or functionality may be implemented or provided in other manners, such as at least partially in firmware and/or hardware, including, but not limited to, one or more application-specific integrated circuits (ASICs), digital signal processors, discrete circuitry, logic gates, standard integrated circuits, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof.

Embodiments of the present disclosure include a device that includes thermal imaging circuitry, which, in operation, executes a sequence of thermal image capture cycles to capture a sequence of thermal images and spectral imaging circuitry, which, in operation, executes a sequence of spectral image capture cycles to capture a sequence of spectral images. The device includes control circuitry, coupled to the thermal imaging circuitry and to the spectral imaging circuitry, where the control circuitry, in operation, synchronizes execution of spectral image capture cycles by the spectral imaging circuitry with execution of thermal image capture cycles by the thermal imaging circuitry. These may all be included on an aerial vehicle in fixed position with respect to each other.

The device includes one or more additional spectral imaging circuits, where the control circuitry, in operation, synchronizes execution of spectral image capture cycles by the one or more additional spectral imaging circuits with the execution of the thermal image capture cycles by the thermal imaging circuitry. The device includes the spectral image circuitry and the one or more additional spectral image circuits have a common shutter. The control circuitry, in operation, generates a digital surface model based on the sequence of spectral images or generates the digital surface model based on the sequence of thermal images.

In other variations, the control circuitry, in operation, generates a composite pixel map of an area of interest based on the digital surface model. The control circuitry, in operation, identifies distressed plants based on the composite pixel map. The distress plants may be identified from a variety of plant properties, such as leaf color and temperature.

The control circuitry, in operation, can estimate temperatures of pixels or groups of pixels in the composite pixel map. The control circuitry, in operation, estimates pixel conditions based on the composite pixel map and the estimated temperatures. In addition, the control circuitry, in operation, identifies plant properties based on the composite pixel map and the estimated temperatures. The device can be an aerial vehicle having a first surface and a second surface opposite the first surface, the aerial vehicle including an irradiance detection device on the first surface, the thermal and spectral imaging devices being on the second surface. In embodiments, the control circuitry synchronizes the spectral image capture cycle with every other thermal image capture cycle. The control circuitry, in operation, identifies conditions consistent with an irrigation leak based on the estimated pixel conditions.

In other embodiments, the present disclosure is directed to a method that includes executing, by a thermal imaging device, a sequence of thermal image capture cycles to capture a sequence of thermal images, synchronizing execution, by a spectral imaging device, of spectral image capture cycles to capture a sequence of spectral images with execution of thermal image capture cycles by the thermal imaging device, and generating a digital surface model of an area of interest based on the sequence of spectral images. The method includes synchronizing execution of spectral image capture cycles by a plurality of spectral imaging devices with the execution of the thermal image capture cycles by the thermal imaging circuitry. The digital surface model is based on the sequence of thermal images. The method also includes generating a composite pixel map of the area of interest based on the digital surface model and can identify distressed plants based on the composite pixel map.

The method includes estimating temperatures of pixels or groups of pixels in the composite pixel map. The method includes estimating pixel conditions based on the composite pixel map and the estimated temperatures. The method also includes identifying irrigation leaks based on the pixel occupancy map and the estimated temperatures. In embodiments, the method includes projecting thermal data onto the digital surface model in response to the sequence of thermal images. The method can store the sequence of thermal images and the sequence of spectral images, a number of the sequence of thermal images being greater than a number of the sequence of spectral images.

Other embodiments include identifying an object in a first one of the spectral images and a second one of the spectral images, identifying first location information associated with the first one of the spectral images and second location information associated with the second one of the spectral images, and generating the digital surface model from at least the first and second ones of the spectral images with the first and second location information. The method may include identifying the object in at least two of the thermal images of the sequence of thermal images by associating a capture time of the first one and the second one of the spectral images with the thermal images of the sequence of thermal images, identifying a measurement for the object for each thermal image, projecting the measurement for the object for each thermal images onto the digital surface model.

Another embodiment includes capturing a plurality of thermal images from a thermal imaging device on an aerial vehicle, the capturing having a first frequency of capture, capturing a plurality of spectral images from a spectral imaging device on the aerial vehicle, the capturing having a second frequency of capture that is less than the first frequency of capture, synchronizing a shutter of the spectral imaging device with the shutter of the thermal imaging device at the second frequency of capture, and generating a digital surface model representative of depth information of an environment being imaged based on the plurality of spectral images. The method includes generating a high resolution thermal overlay of the digital surface model by identifying a physical object imaged in the plurality of spectral images, depth information of the physical object being presented as a point in the digital surface model, identifying a subset of the plurality of thermal images by aligning the first frequency of capture with the synchronized second frequency of capture, identifying the object in the subset of the plurality of thermal images, identifying a plurality of thermal information data measurements regarding the object in the subset of the plurality of thermal images, and projecting the plurality of thermal information data measurements onto the point associated with the object in the digital surface model.

The present disclosure is also directed to a device that includes thermal imaging circuitry, which, in operation, executes a sequence of thermal image capture cycles to capture a sequence of thermal images, spectral imaging circuitry, which, in operation, executes a sequence of spectral image capture cycles to capture a sequence of spectral images, inertial motion sensing circuitry, which, in operation, generates data indicative of relative movement of the device, and control circuitry, coupled to the thermal imaging circuitry, to the spectral imaging circuitry, and to the inertial motion sensing circuitry. The control circuitry, in operation: synchronizes execution of spectral image capture cycles by the spectral imaging circuitry with execution of thermal image capture cycles by the thermal imaging circuitry and estimates a pose of a thermal image of the sequence of thermal images based on the data indicative of relative movement of the device.

The inertial motion sensing circuitry may be an accelerometer or a gyroscope. The control circuitry, in operation, generates a digital surface model based on the sequence of spectral images. The control circuitry, in operation, generates the digital surface model based on the sequence of thermal images. The control circuitry, in operation, generates the digital surface model based on the estimated pose of the thermal image.

An alternative embodiment is directed to a method that includes executing, by a thermal imaging device, a sequence of thermal image capture cycles to capture a sequence of thermal images, synchronizing execution, by a spectral imaging device, of spectral image capture cycles to capture a sequence of spectral images with execution of thermal image capture cycles by the thermal imaging device, capturing inertial motion data with an inertial motion sensor, estimating a pose of a thermal image in the sequence of thermal images based on the captured inertial motion data, and generating a digital surface model of an area of interest based on the sequence of spectral images. The thermal imaging device, the spectral imaging device, and the inertial motion sensor are fixed with respect to each other on an aerial device. The method includes capturing depth and thermal information about the area with the thermal imaging device and the spectral imaging device. The method also includes identifying an object from the area in the sequence of spectral images, generating a point on the digital surface model representative of the object based on the sequence of spectral images, generating a plurality of thermal measurements from the sequence of thermal images associated with the object, projecting each of the plurality of thermal measurements on the point on the digital surface model.

The method further includes correlating the plurality of thermal measurements from the sequence of thermal images by associating the inertial measurement data with each thermal image. It may also include capturing inter-frame location information with the inertial measurement data and correlating the inter-frame location information with each thermal images of the sequence of thermal images.

Another embodiment is a device or unmanned aerial vehicle that includes thermal imaging circuitry, which, in operation, executes a sequence of thermal image capture cycles to capture a sequence of thermal images, spectral imaging circuitry, which, in operation, executes a sequence of spectral image capture cycles to capture a sequence of spectral images, and control circuitry, coupled to the thermal imaging circuitry, to the spectral imaging circuitry. The control circuitry, in operation gathers irradiance data indicative of a background temperature, synchronizes execution of spectral image capture cycles by the spectral imaging circuitry with execution of thermal image capture cycles by the thermal imaging circuitry, generates a digital surface model based on the sequence of spectral images, estimates an emissivity of a target, and estimates a temperature of a pixel of the digital surface model based on the sequence of thermal images, the irradiance data indicative of the background temperature and the estimated emissivity of the target.

The irradiance sensing circuitry includes a plurality of photo sensors. The plurality of photo sensors are configured to simultaneously sense irradiance from a light source, where the light source is the sun. The irradiance sensing circuitry, which, in operation, senses irradiance data indicative of the background temperature. The control circuitry gathers the irradiance data from an irradiance model based on environmental conditions. The control circuitry gathers the irradiance data from an irradiance model based the sequence of spectral images. The control circuitry gathers the irradiance data from an irradiance model based the sequence of thermal images. The control circuitry gathers the irradiance data from an irradiance model based the sequence of spectral images and the sequence of thermal images.

Another method includes capturing a sequence of thermal images with thermal imaging circuitry by executing a sequence of thermal image capture cycles, capturing a sequence of spectral images with spectral imaging circuitry by executing a sequence of spectral image capture cycles, and processing the sequence of spectral images and the sequence of thermal images with control circuitry coupled to the thermal imaging circuitry and to the spectral imaging circuitry. The processing includes estimating irradiance data indicative of a background temperature, synchronizing the capturing of the spectral image capture cycles by the spectral imaging circuitry with the capturing of thermal image capture cycles by the thermal imaging circuitry, the capturing of the thermal image capture cycles being more frequent than the spectral image capture cycles, generating a digital surface model based on the sequence of spectral images, estimating an emissivity of a target, and estimating a temperature of a pixel of the digital surface model based on the sequence of thermal images, the irradiance data indicative of the background temperature and the estimated emissivity of the target.

The method includes the estimating of the irradiance data includes capturing irradiance data with an irradiance data capture device positioned on a first surface of an aerial vehicle, the spectral imaging circuitry and the thermal imaging circuitry being on a second surface of the aerial vehicle that is opposite to the first surface. The method includes the estimating of the irradiance data includes capturing irradiance data with an irradiance data capture device positioned facing a first direction, the spectral imaging circuitry and the thermal imaging circuitry positioned facing a second direction that is different from the first direction. The estimating of the emissivity includes generating the irradiance data from the spectral images. The estimating of the emissivity includes generating the irradiance data from the thermal images. The estimating of the emissivity includes generating the irradiance data from the spectral images and the thermal images.

The disclosure also includes a method of executing, by a thermal imaging device, a sequence of thermal image capture cycles to capture a sequence of thermal images; synchronizing execution, by a spectral imaging device, of spectral image capture cycles to capture a sequence of spectral images with execution of thermal image capture cycles by the thermal imaging device; sensing irradiance data indicative of a background temperature; generating a digital surface model based on the sequence of spectral images; estimating an emissivity of a target; and estimating a temperature of a pixel of the digital surface model based on the sequence of thermal images, the irradiance data indicative of the background temperature and the estimated emissivity of the target.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/774,814 filed Dec. 3, 2018, U.S. Provisional Patent Application No. 62/774,815 filed Dec. 3, 2018, and U.S. Provisional Patent Application No. 62/774,812 filed Dec. 3, 2018, are incorporated herein by reference, in their entirety. Aspects of the embodiments can be modified, if necessary to employ concepts of the various embodiments and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
thermal imaging circuitry, which, in operation, executes a sequence of thermal image capture cycles to capture a sequence of thermal images;
spectral imaging circuitry, which, in operation, executes a sequence of spectral image capture cycles to capture a sequence of spectral images;
inertial motion sensing circuitry, which, in operation, generates data indicative of relative movement of the device; and
control circuitry, coupled to the thermal imaging circuitry, to the spectral imaging circuitry, and to the inertial motion sensing circuitry, wherein the control circuitry, in operation:
synchronizes execution of spectral image capture cycles by the spectral imaging circuitry with execution of thermal image capture cycles by the thermal imaging circuitry; and
estimates a pose of a thermal image of the sequence of thermal images based on the data indicative of relative movement of the device.

2. The device of claim 1 wherein the inertial motion sensing circuitry comprises an accelerometer.

3. The device of claim 1 wherein the inertial motion sensing circuitry comprises a gyroscope.

4. The device of claim 1 wherein the control circuitry, in operation, generates a digital surface model based on the sequence of spectral images.

5. The device of claim 4 wherein the control circuitry, in operation, generates the digital surface model based on the sequence of thermal images.

6. The device of claim 5 wherein the control circuitry, in operation, generates the digital surface model based on the estimated pose of the thermal image.

7. A method, comprising:
executing, by a thermal imaging device, a sequence of thermal image capture cycles to capture a sequence of thermal images;
synchronizing execution, by a spectral imaging device, of spectral image capture cycles to capture a sequence of spectral images with execution of thermal image capture cycles by the thermal imaging device;
capturing inertial motion data with an inertial motion sensor;
estimating a pose of a thermal image in the sequence of thermal images based on the captured inertial motion data; and
generating a digital surface model of an area of interest based on the sequence of spectral images.

8. The method of claim 7 wherein the thermal imaging device, the spectral imaging device, and the inertial motion sensor are fixed with respect to each other on an aerial device.

9. The method of claim 7, further comprising capturing depth and thermal information about the area with the thermal imaging device and the spectral imaging device.

10. The method of claim 9, further comprising:
identifying an object from the area in the sequence of spectral images;
generating a point on the digital surface model representative of the object based on the sequence of spectral images;
generating a plurality of thermal measurements from the sequence of thermal images associated with the object;
projecting each of the plurality of thermal measurements on the point on the digital surface model.

11. The method of claim 10, further comprising:
correlating the plurality of thermal measurements from the sequence of thermal images by associating the inertial measurement data with each thermal image.

12. The method of claim 7, further comprising capturing inter-frame location information with the inertial measurement data and correlating the inter-frame location information with each thermal images of the sequence of thermal images.

13. A method, comprising:
capturing a sequence of thermal images with thermal imaging circuitry by executing a sequence of thermal image capture cycles;
capturing a sequence of spectral images with spectral imaging circuitry by executing a sequence of spectral image capture cycles; and
processing the sequence of spectral images and the sequence of thermal images with control circuitry coupled to the thermal imaging circuitry and to the spectral imaging circuitry, the processing including:
estimating irradiance data indicative of a background temperature;
synchronizing the capturing of the spectral image capture cycles by the spectral imaging circuitry with the capturing of thermal image capture cycles by the thermal imaging circuitry, the capturing of the thermal image capture cycles being more frequent than the spectral image capture cycles;
generating a digital surface model based on the sequence of spectral images;
estimating an emissivity of a target; and
estimating a temperature of a pixel of the digital surface model based on the sequence of thermal images, the irradiance data indicative of the background temperature and the estimated emissivity of the target.

14. The method of claim 13 wherein the estimating of the irradiance data includes capturing irradiance data with an irradiance data capture device positioned on a first surface of an aerial vehicle, the spectral imaging circuitry and the thermal imaging circuitry being on a second surface of the aerial vehicle that is opposite to the first surface.

15. The method of claim 13 wherein the estimating of the irradiance data includes capturing irradiance data with an irradiance data capture device positioned facing a first direction, the spectral imaging circuitry and the thermal imaging circuitry positioned facing a second direction that is different from the first direction.

16. The method of claim 13 wherein the estimating of the emissivity includes generating the irradiance data from the spectral images.

17. The method of claim 13 wherein the estimating of the emissivity includes generating the irradiance data from the thermal images.

18. The method of claim 13 wherein the estimating of the emissivity includes generating the irradiance data from the spectral images and the thermal images.

19. The method of claim 13, comprising estimating pixel conditions based on an estimated temperature from the estimating the temperature of the pixel.

20. The method of claim 19, comprising identifying irrigation leaks based on a pixel occupancy map and the estimated temperature.

* * * * *